United States Patent

Busch

[11] Patent Number: 6,167,294
[45] Date of Patent: Dec. 26, 2000

[54] METHOD AND APPARATUS FOR PRODUCING BENEFIT/RISK EVALUATION DATA RELATING TO RADIATION THERAPY IN PATIENTS

[76] Inventor: Martin Busch, Auenstrasse 3a, 82275 Emmering, Germany

[21] Appl. No.: 08/973,155

[22] PCT Filed: Feb. 3, 1997

[86] PCT No.: PCT/EP97/00463
§ 371 Date: May 4, 1998
§ 102(e) Date: May 4, 1998

[87] PCT Pub. No.: WO97/36648
PCT Pub. Date: Oct. 9, 1997

[30] Foreign Application Priority Data

Mar. 29, 1996 [DE] Germany ............ 196 12 668

[51] Int. Cl.$^7$ ...................................... A61B 6/00
[52] U.S. Cl. .................. 600/425; 600/436; 128/924; 364/275.7; 364/274.5
[58] Field of Search ................... 600/425, 436; 128/920, 922, 924, 925; 395/10, 20, 50; 364/274, 274.2, 274.5, 274.7, 275.7, 922, 922.2; 378/64, 65

[56] References Cited

U.S. PATENT DOCUMENTS

| | | | |
|---|---|---|---|
| 4,884,217 | 11/1989 | Skeirik et al. ............... | 364/513 |
| 5,205,289 | 4/1993 | Hardy et al. ............... | 128/653.1 |
| 5,339,812 | 8/1994 | Hardy et al. ............... | 128/653.1 |
| 5,391,139 | 2/1995 | Edmundson .................. | 600/7 |
| 5,458,125 | 10/1995 | Schweikard ................. | 128/653.1 |
| 5,511,549 | 4/1996 | Legg et al. ................. | 128/653.1 |
| 5,513,238 | 4/1996 | Leber et al. ................ | 378/65 |
| 5,602,892 | 2/1997 | Llacer ...................... | 378/65 |
| 5,647,663 | 7/1997 | Holmes ..................... | 128/653.1 |
| 5,672,154 | 9/1997 | Sillen et al. ............... | 604/50 |
| 5,815,547 | 9/1998 | Shepard et al. ............. | 378/65 |

FOREIGN PATENT DOCUMENTS

| | | | |
|---|---|---|---|
| WO 91/18552 | 12/1991 | WIPO | A61B 6/00 |
| WO 95/20354 | 8/1995 | WIPO | A61B 6/00 |

OTHER PUBLICATIONS

Schneider, Uwe, "Proton Radiography as a Tool for Quality Control in Proton Therapy," Med. Phys. 22(4), Apr. 1995, Woodbury, New York.

Venselaar, J.L.M., "Measurement and Calculation of the Dose at Large Distances from Brachytherapy Sources: Cs–137, 1r–192, and Co–60," Med. Phys. 23(4), Apr. 1996.

*Primary Examiner*—Marvin M. Lateef
*Assistant Examiner*—Shawna J Shaw
*Attorney, Agent, or Firm*—Michael J. Donohue; Seed IP Law Group PLLC

[57] ABSTRACT

Process for producing benefit/risk evaluation data relating to radiation therapy in patients comprising the following stages: production of imaga data on the spatial positional distribution of relevant organ and tissue parts; production or selection of radiation data; production of radiation dose distribution data; storage of a plurality first rules; fetching of suitable first rules; storage of a plurality of second rules; fetching and application of suitable second rules; production of benefit/risk evaluation data based on the total radiation effect data produced; and fetching of suitable radiation data.

10 Claims, 1 Drawing Sheet

METHOD AND APPARATUS FOR PRODUCING BENEFIT/RISK EVALUATION DATA RELATING TO RADIATION THERAPY IN PATIENTS

BACKGROUND OF THE INVENTION

The present invention relates to a method and an apparatus for producing benefit/risk evaluation data relating to radiation therapy in patients.

It is the goal of clinical radiation therapy to cure patients of tumor diseases and, at the same time, to avoid side-effects as much as possible. Therefore, when a radiation plan is worked out, it is important that the clinical effects of the radiation doses in patients are judged with foresight and that the radiation plan which is used in the end is chosen in compliance with a benefit/risk evaluation made.

Therefore, a suitable radiation plan will adapt the used radiation fields to predetermined tumor contours and also take into account the simultaneously effected radiation of healthy tissue and possible damage caused thereby. This is necessary since for physical reasons a homogeneous dose distribution over the target volume alone, i.e. the tumor to the irradiated, is not possible, but healthy tissue and healthy organs are also irradiated, the tissue and organs being sometimes very prone to radiation damage.

To help a surgeon in choosing a suitable radiation plan, it is nowadays already common practice to predict a specific radiation plan-effected dose distribution in the patient's tissue by way of calculations. To be more specific, it is known that so-called isodose plans are made, on the basis of which the surgeon can read the places of equally high radiation doses, similar to isobars on a weather map.

On the basis of the distribution of the radiation doses in the body and, in particular, on the basis of knowledge about radiation doses in risky organs and tissue parts, the surgeon can draw up a radiation plan in which it is at least ensured that radiation-sensitive organs and tissue parts, in particular, are not unnecessarily stressed in relation to the achieveable success.

When drawing up a radiation plan which is suited in the present sense, the surgeon will thus rely on his clinical experience and on the literature known to him, which gives him information about the extent to which specific doses are acceptable for individual organs in comparison with the achieveable benefit for the patient. Of course, every surgeon will thus develop a radiation plan determined by his own personal knowledge, and such a radiation plan will of course only be based on a rough benefit/risk estimation.

Particularly in consideration of today's technical possibilities of spatially representing a radiation dose distribution to be expected in a patient's body, it becomes apparent that it is very difficult for a radiologist to convert the information available to him about the radiation dose distribution in a correct manner into the corresponding biological affects, based on the knowledge he has access to, and thus to carry out a reliable benefit/risk estimation.

To make the selection among suitable radiation plans easier for the surgeon, it is also known that so-called dose volume histograms are prepared for specific organs on the basis of the calculated spatial radiation dose distribution. Such a dose volume histogram informs the surgeon under loss of the spatial resolution which percentages of a specific organ are respectively stressed by which radiation doses. Such a conversion into dose volume histograms helps the surgeon to exploit the causal effects known to him from the medical literature or his practical clinical experience for this risk/benefits estimation.

For instance, starting from such a dose volume histogram, the surgeon can draw the conclusion that he should prefer a radiation plan with a relatively uniform radiation load for a specific organ, of which the surgeon knows, however, that the radiation is not very likely to damage the relevant organ, to a radiation plan in the case of which the same organ is less stressed on the whole, but loaded in some places with radiation doses that are very likely to cause later damages.

Hence, in consideration of such dose volume histograms and in view of the whole literature that is available in the field of radiotherapy, the surgeon can make a statement for each individual organ as to whether or not a specific radiation plan will be acceptable for the organ concerned. However, since it is already impossible for reasons of time to consider the whole available knowledge for each individual organ and to select, on the basis thereof, the radiation plan that represents the best compromise between various benefit/risk evaluations made, it is normally just the knowledge available to the surgeon that in clinical practice influences the preparation of the radiation plan, with arbitrary or instinctive decisions also playing a role in the final choice of the radiation plan.

SUMMARY OF THE INVENTION

It is the object of the present invention to provide a method and an apparatus with the aid of which a benefit/risk evaluation relating to radiation therapy in patients can be carried out in an easy and reliable manner.

This object is achieved, on the one hand, by a method for producing benefit/risk evaluation data relating to radiation therapy in patients with the following steps:

a) producing image data on the spatial positional distribution of relevant organ and tissue parts;

b) producing or selecting radiation data determining a suitable radiation for the patient, based on the image data on the spatial positional distribution of relevant organ and tissue parts, and based on the intended therapy;

c) producing radiation dose distribution data which, based on the image and radiation data produced, represent a spatial distribution of the applied physical radiation doses with respect to the relevant organ and tissue parts;

d) storing a plurality of first rules which indicate correlations between therapeutic effects and/or side-effects on the one hand and applied physical radiation doses on the other hand;

e) fetching suitable first rules and applying said rules to individual organ and/or tissue volume units of the relevant organ and /or tissue parts and, based thereon, producing biological radiation effect data for the individual volume units;

f) storing a plurality of second rules which describe correlations between the biological radiation effect data determined for the individual volume parts of a tissue or organ part and total effects and/or total side-effects to be expected for the relevant tissue or organ part;

g) fetching and applying suitable second rules to the biological radiation effect data produced and producing organ and/or tissue-specific biological total radiation affect data;

h) producing benefit/risk evaluation data, based on the total radiation effect data produced;

i) repeating at least some of steps b), c), e), g), h) and j) selecting those radiation data for the therapy to be performed that, in comparison with other radiation data, have led to the most suited benefit/risk evaluation data.

This object is achieved, on the other hand, by an apparatus for producing benefit/risk evaluation data relating to radiation therapy in patients, comprising the following devices:

- a computer tomography device for producing and storing image data representing the spatial positional distribution of relevant tissue and organ parts;
- a device for producing radiation data on the basis of which a patient can be irradiated by a radiation means, the data being produced in response to the data produced by the computer tomography device;
- a device for producing radiation dose distribution data which represent a simulated dose distribution in the relevant tissue and organ parts in cases of a radiation therapy in patients based on radiation data;
- a rule-based expert system containing a first set of rules and a second set of rules, said first set of rules concerning correlations between therapeutic effects and/or side-effects on the one hand and applied physical radiation doses on the other hand and the expert system applying the first set of rules to the produced radiation doses in terms of individual volume units of the relevant tissue and organ parts and producing corresponding biological radiation effect data for the individual volume parts, and the second set of rules describing correlations between the biological radiation effect data determined for the individual volume parts of a tissue to organ part and total effects and/or total side-effects to be expected for the relevant tissue organ part, and the expert system applying the second set of rules to the biological radiation effect data for the individual volume parts of a tissue organ part and, based thereon, benefit/risk evaluation data for the relevant tissue or organ part.

The present invention is based on the finding that in former procedures regarding radiation planning the existing knowledge about tissue- and organ-specific effects of specific radiation doses has been exploited in an inadequate manner. Furthermore, the present invention is based on the finding that only a computer-aided approach can be successful with respect to a reliable evaluation of the biological effects of a radiation treatment, but such an approach should not be based on a mathematical model because this would presuppose clear causal connections for the success, such connections, however, being not found in clinical practice.

Therefore, according to the invention, use should particularly be made in any desired detailed manner of the knowledge presented in medical publications and regarding individual biological effects of radiation doses, namely in the form of a rule-based expert system which radiation plans are assessed. With today's available computer powers, it is theoretically possible to fetch the whole available knowledge within a short period of time and to make use of it when making an assessment as to which biological effects are developed by a specific spatial radiation dose distribution.

Furthermore, the invention is based on the finding that it is necessary for a reliable and exact total assessment that an assessment should first be made of individual volume parts of the irradiated area and that the biological total effect, based on the individual affects determined for the individual volume parts, should subsequently be evaluated for each organ or each tissue section. Hence, in contrast to an evaluation be means of a dose volume histogram, the spatial radiation dose distribution has some influence on the total assessment, and it is not only dose distribution percentages in a specific organ or tissue section that are taken into account.

According to a preferred embodiment of the present invention the expert system used can manage with rules that are subject to uncertainty, preferably employing an approach underlying the fuzzy-set theory.

Such an approach based on the fuzzy-set theory seems to be particularly suited, since it can apply the incomplete and fuzzy knowledge found in the literature in an optimum manner to any desired constellations that exist in practice.

Further preferred embodiment of the present invention are the subject matter of the subclaims.

Figure 1:
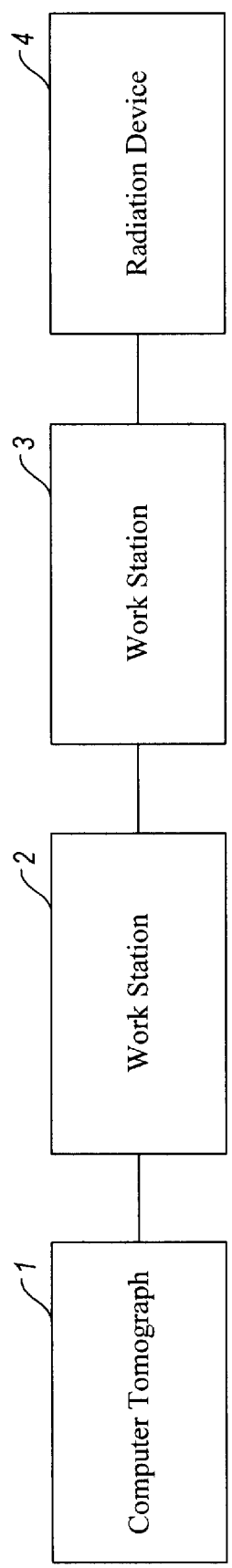
FIG. 1 is a functional block diagram representative of the present invention.

Preferred embodiments of the present invention shall now be explained in detail in the following text, partly with reference to the attached drawing.

DETAILED DESCRIPTION OF THE INVENTION

To be able to determine the target volume to be irradiated and to image the radiation dose distribution caused by a specific radiation plan, image data are first produced on the spatial distribution of the relevant organ and tissue parts of a patient. The data are preferably produced by means of a computer tomograph or MR tomograph 1 illustrated in the drawing, which scans the relevant part of the patient's body and supplies the corresponding image data.

On the basis of the image data gained, a rough radiation plan is then chosen by means of which the target volume to be irradiated can be irradiated with the load on the neighboring volumes being as small as possible. Such initial radiation plans can directly be made a computer unit 2, based on the image data supplied by the computer tomograph 1. Starting from the radiation plan used, the computer unit 2 will then calculate the physical radiation dose distribution over a patient's individual organ and tissue parts of interest. The spatial radiation distribution data produced in this manner can be displayed graphically and inform the radiologist, preferably by way of different stainings, about the physical radiation dose distribution affected on the patient.

Based on the radiation dose distribution data, a rule-based expert system which is implemented on a computer unit 3 calculates the corresponding biological radiation effect data for each individual volume element of the irradiated body section.

To this end, the expert system stores a plurality of rules regarding correlations between therapeutic effects and/or side-effects on the one hand and applied physical radiation doses on the other hand. The corresponding rules are here gained from the available literature and from clinical practice. The expert system applies these rules to individual volume elements, for example to every com of the irradiated volume, and calculates biological radiation effect data therefrom for each relevant volume element.

This means that during the conversion of the physical radiation dose distribution into biological effect data the spatial radiation dose distribution is taken into account in an inventive manner. in a second step, the expert system will then determine biological total effect data for each tissue or organ or organ part and for each tissue section to be considered as a unit. These data contain information about the total biological effect for the relevant organ or the relevant tissue section, based on the individual effects in the individual volume elements of the corresponding organ or tissue section.

The expert system achieves such a conversion of individual volume data into data on the total volume of the organ or the organ section to be jointly considered by applying a further set of rules which, in turn, are again obtained from the available literature or from clinical practice.

This further set of rules may, for instance, take into consideration whether a relevant organ in a so-called "serial" or "parallel" organ, in the case of a parallel organ, such as the lung or the kidney, radiation damage that is confined to a selected piece or spot has no effect on the function of the whole organ. Hence, high doses that are confined to a selected place or spot as well as corresponding injuries that are confined to a selected place or spot are acceptable in the case of such organs. In the case of serial organs, such as the spinal marrow or the brain stem, damages that are confined to a selected place or spot can already effect serious malfunctions. Hence, with such organs, selectively high radiation doses having correspondingly great biological effects should never be applied so as to maintain the whole functional ability. Depending on the base, however, homogeneous doses applied to a considerable or average degree are acceptable in such organs, provided that individual threshold doses are not exceeded. Based on tumor tissue, a minimum radiation dose must be ensured to give the patient a change of healing.

Such knowledge is taken into account by the expert system for applying the biological effect data of individual volume units to healthy organ parts or coherent tissue sections.

Based on the total effect data determined in this manner, it is then possible to carry out a benefit/risk evaluation for the corresponding organs or tissue sections of interest.

Based on such a benefit/risk evaluation, a suitable radiation plan can then be chosen among a plurality of possible irradiation plans. The biological total effect data or the benefit/risk evaluations can also be used for drawing up or adapting a suitable radiation plan. In such a case, the computer unit 3 would return its results to unit 2 so that the latter can draw up the suitable radiation plan.

Preferably, the biological total effect data are separately determined for each organ and each tissue section to be considered as a unity, and such a separate benefit/risk evaluation is carried out. In a third step, the expert system can then compare the individual benefit/risk considerations with one another and, based thereon, choose the best suited radiation plan. Such a choice can again be made on the basis of corresponding rules known in the literature or from clinical practice.

Preferably, the computer unit 3 is capable of representing the prepared benefit/risk evaluations graphically so that the patient can also see which risks he is running with a planned radiation in relation to the achievable therapeutic success.

On the basis of the radiation plan chosen by the expert system 3, the patient can then be irradiated by a radiation device 4. The radiation device 4 is preferably connected via a network to the expert system and can fetch the relevant data from the expert system.

The expert system operates in a specifically preferred manner on the basis of the so-called fuzzy-set theory approach and thus with rules that are subject to some uncertainty. This approach seems to be best suited for applying the incomplete knowledge known from literature and practical radiation therapy to any situation that arises in practice.

The fuzzy-set theory is concerned with "fuzzy sets" whose elements belong to individual sets in different ways. While in the classical theory of sets a specific element does or does not belong to a set, the fuzzy-set theory deals with elements that only belong to a set to a certain degree. The degree of belonging is indicated by a function for the individual elements of a set. With the approach, it is possible to make decisions based on incomplete knowledge and in the absence of exactly measured input values. Fuzzy systems are capable of operating in a stable manner even in the case of contradictory individual rules.

An example of a rule that could be applied by the expert system in the first step, i.e., could belong to the first set of rules is, for example, the following rule:

"When the single dose in a lung part element amounts to 2 Gy and the total dose to 40 Gy, when the period of application is four weeks, when no breaks are made and when a specific toxic chemotherapy is performed at the same time and the patient has a predamaged lung due to silicosis, the damage inflicted by the radiation therapy in a lung part element will be high".

Thus, the damage is linguistically classified more or less accurately, for instance, by "no", "small", "average", "high", "total". Such rules must exist for each organ or tissue individually and should also exist for different doses, if possible 500 rules are taken into account in the above-mentioned first step in a prototype of the system developed by the inventor. The rules are then linked with the aid of fuzzy mathematics.

According to the invention these rules are applied to volume parts having, for instance, a size of 1 ccm. It is preferably checked to which extent an actually existing situation corresponds to the prerequisites (left sides) of the existing rules. A degree of compatibility is calculated therefrom for each existing rule. The compatibility degrees are then added to the results (right sides) of the rules. This leads to a list of results which are more or less true (depending on compatibility with the input parameters). Rules whose degree of compatibility is zero will no longer be considered. The aggregation of all "evaluated" results is made either by minimum consideration or by multiplication. As a result, one obtains a fuzzy set which furnishes information on the tissue damage. To be more specific, the result set indicates which ones of the many possible damage degree are present to which extent for the relevant volume element.

Subsequently, a second evaluation is made, based on a second set of rules. Using the fuzzy set theory again, the individual fuzzy sets which are present for a single organ are added. As mentioned, one obtains for each organ, or for each tissue section to be considered as a unit, a biological total effect on the basis of which a benefit/risk evaluation can then be made.

Since considerable computing efforts are required in the presence of extensive sets of rules and, in particular, upon application of the first set of rules to each individual volume element, a preferred embodiment provides that only representative points of the radiated body section should be used for the calculation. For instance, only 400 statistically distributed and representative volume elements can be considered in the whole irradiated volume or in an organ of interest. With the use of such subsets, the computational efforts can be reduced considerably, so that the benefit/risk evaluation can be made within a very short period of time and can be present, so to speak, "at the same time" as the prepared isodose distribution. According to the invention the first rules can also be applied to dose volume histograms instead of or in addition to the individual volume elements, it is here necessary that the dose volume histograms based on the radiation dose distribution data are first prepared for each organ, organ part or each tissue section. The expert system will then apply a first set of rules to the dose volume histograms prepared in this manner to produce the biological radiation effect data for the corresponding organs, organ parts or tissue sections.

As already mentioned above, the benefit/risk evaluation data are preferably determined separately for each organ or each tissue section. These separate benefit/risk evaluation data are subsequently converted in a further step by the expert system into benefit/risk evaluation data for the whole body, the operation being again performed by applying correspondingly suitable rules.

What is claimed is:

1. A method of producing benefit/risk evaluation data relating to an intended radiation therapy in patients, comprising the following steps:

a) producing image data on a spatial positional distribution of relevant anatomical regions;

b) producing radiation data which determine a suitable radiation therapy for patients, based on the image data on the spatial positional distribution and on an intended therapy, c) producing radiation dose distribution data which, based on the image and radiation data produced, represent a spatial distribution of applied physical radiation doses with respect to the relevant anatomical regions;

d) storing a plurality of first rules which indicate correlations between radiation effects and applied physical radiation doses;

e) applying at least one of said plurality of first rules to volume units of the anatomical regions and, based thereon, producing biological radiation effect data for the volume units;

f) storing a plurality of second rules which describe correlations between the biological radiation effect data and total effects to be expected for the relevant anatomical regions;

g) applying at least one of the plurality of second rules to the biological radiation effect data produced, and producing biological total radiation effect data;

h) producing benefit/risk evaluation data based on the total radiation effect data produced; and i) selecting those radiation data for the therapy to be performed that, in comparison with the other radiation data, have led to the most suited benefit/risk evaluation data.

2. The method according to claim 1 wherein steps d) and e), on the one hand, and steps f) and g), on the other hand, are each carried out by an expert system.

3. The method according to claim 2 wherein the expert system performing steps d) and e) operates with rules that are subject to uncertainty, and utilizes fuzzy-set theory.

4. The method of claim 1 wherein step c) comprises the preparation of dose-volume histograms.

5. The method of claim 1 wherein the benefit/risk evaluation data are produced individually for each organ or tissue part of the relevant anatomical regions.

6. The method of claim 1 wherein only a subset of the volume units contained in the relevant anatomical regions is taken into account for data generation.

7. An apparatus for producing benefit/risk evaluation data relating to radiation therapy in patients, comprising:

a computer tomography device for producing and storing image data which represent a spatial positional distribution of relevant tissue and organ parts;

a device for producing radiation data on the basis of which a patient can be irradiated by a radiation device, the radiation data being produced in response to the image data;

a device for producing radiation dose distribution data which represent a simulated dose distribution in the relevant tissue and organ parts in the case of radiation therapy in patients based on the radiation data;

a rule-based expert system containing a first set of rules and second set of rules, said first set of rules regarding correlations between radiation effects and applied physical radiation doses, the expert system applying the first set of rules to the produced radiation doses in terms of individual volume units of the relevant tissue and organ parts and thereby producing corresponding biological radiation effect data for the individual volume parts, and the second set of rules describing correlations between the biological radiation effect data determined for the individual volume parts of a tissue or organ part and total radiation effects to be expected for the relevant tissue or organ part, and the expert system applying said second set of rules to the biological radiation effect data for the individual volume parts of a tissue or organ part to produce biological total radiation effect data for the corresponding tissue or organ part and, based thereon, benefit/risk evaluation data for the corresponding tissue or organ part.

8. An apparatus according to claim 7 wherein the expert system operates with rules that are subject to uncertainty and utilizes fuzzy-set theory.

9. The apparatus of claim 7 wherein the expert system selects the suitable radiation data relating to radiation therapy in patients, based on the total radiation effect data and a benefit/risk evaluation based thereon.

10. The apparatus of claim 7, further comprising a radiation device for radiation therapy in patients.

* * * * *